United States Patent [19] [11] 4,230,239
Birrell [45] Oct. 28, 1980

[54] CYCLICALLY OPERABLE DISPENSER PROVIDING A DOUBLE CLOSURE BETWEEN DISPENSING CYCLES

[75] Inventor: Peter L. Birrell, South Delta, Canada
[73] Assignee: Acro-Matic, Inc., Warrington, Pa.
[21] Appl. No.: 886,192
[22] Filed: Mar. 13, 1978
[51] Int. Cl.³ .............................................. G01F 11/28
[52] U.S. Cl. .................. 222/185; 222/440; 222/448; 222/449; 222/547
[58] Field of Search ...................... 222/41, 47, 48, 158, 222/181, 185, 437, 438, 439, 440, 447, 449, 450, 460, 462, 547, 564

[56] References Cited
U.S. PATENT DOCUMENTS

| 1,988,865 | 1/1935 | Campbell | 222/181 |
| 2,054,881 | 9/1936 | Saunders | 222/185 |
| 2,585,299 | 2/1952 | Cook | 222/449 X |
| 2,655,290 | 10/1953 | Mansperger | 222/181 |
| 2,751,128 | 6/1956 | Prince | 222/181 X |
| 2,778,529 | 1/1957 | Appel | 222/440 X |
| 2,852,170 | 9/1958 | Reynolds | 222/439 |
| 3,101,159 | 8/1963 | Fletcher | 222/440 X |
| 3,938,639 | 2/1976 | Birrell | 222/294 X |

FOREIGN PATENT DOCUMENTS

548298 9/1956 Italy .......................... 222/447

Primary Examiner—Robert J. Spar
Assistant Examiner—Fred A. Silverberg
Attorney, Agent, or Firm—Robert J. Mooney

[57] ABSTRACT

Apparatus for dispensing flowable particulate materials from a storage container while protecting the material from unnecessary exposure to ambient atmosphere through a double vapor control mechanism. The apparatus includes a funnel unit mounted below the container for receipt of particulate material therefrom. A flow control disc is mounted between the container and the funnel unit to control the flow of material into the funnel unit, irrespective of the head of material within the funnel. A hollow, moveable, metering bell, and moveable funnel outlet closure are mounted on a common reciprocable rod within the funnel and are normally seated between cycles to provide double isolation of the material from the ambient atmosphere. The metering bell is arranged to be raised by the reciprocable rod in conjunction with a cam mechanism a predetermined, and adjustable, height above the bottom of the funnel unit to permit the particulate material to flow around the bell into the bottom of the funnel until the material reaches its angle of repose. The reciprocable rod is arranged to be pulled downward manually to cause the bell to trap a measured quantity of particulate materials within a dispensing chamber formed between it and the bottom of the funnel. Continued downward movement of the rod moves the closure out of the funnel outlet to enable the material trapped within the dispensing chamber to drop thereout and into a receiving vessel. Release of the rod carries the closure back into the funnel outlet to seal the now empty dispensing chamber. An actuable mechanism is provided to return the bell to the same, or new position, above the bottom of the funnel unit to recharge the apparatus for the next dispensing cycle.

9 Claims, 12 Drawing Figures

CYCLICALLY OPERABLE DISPENSER PROVIDING A DOUBLE CLOSURE BETWEEN DISPENSING CYCLES

This invention relates generally to dispensing apparatus and more particularly to dispensing hygroscopic particulate material.

A great number of apparatus for dispensing particulate and other material, such as foodstuffs, laundry and soap powders, animal feeds, etc., have been disclosed in the patent literature and some such apparatus are commercially available. Examples of various types of prior art apparatus for dispensing flowable particulate materials are found in U.S. Pat. Nos. 502,124 (Keeler), 1,004,855 (Daniels), 1,270,262 (Buckland), 1,631,430 (Schreiber), 1,913,767 (Mills), 2,097,813 (Gollings), 2,227,706 (Connor), 2,405,155 (Packwood, Jr.), 2,503,886 (Olson), 2,597,083 (Dramer), 2,709,543 (Appel), 2,852,170 (Reynolds), 2,778,529 (Appel), 2,873,050 (Halverson), 3,756,497 (Croyle, et al), 3,828,973 (Birrell), and 3,938,639 (Birrell).

Hygroscopic materials such as spray and freeze dried instant coffees, teas, soups, cold drink bases, non dairy creamers, sweeteners, etc., commonly have a virtually unmeasurable moisture content when they are processed and packaged. Such foodstuffs are extremely susceptible to deterioration when exposed to the ambient atmosphere and its attendant moisture content. When these foodstuffs, which flow freely from the processor's original container, are subjected to traditional modes of dispensing by prior art apparatus that do not sustain the product in sealed containers, various mechanical devices must be employed to propel less than the original container-fresh materials through the apparatus. For example, prior art dispensers capable of sustaining trouble-free delivery of hygroscopic materials require connection to energy consuming support systems to create a heated and therefore dry environment at the dispenser delivery port to prevent deterioration, and subsequent malfunction of the apparatus.

The sensitivity of existing, and new developing foodstuffs to ambient atmosphere is such that prior art dispensing apparatus are not suitable for common use in the home environment.

In addition, many prior art apparatus, while ostensibly permitting portion control, have failed to attain the degree of measurement accuracy which is achieved in the typical home environment using standard measuring techniques. While some prior art dispensing apparatus exhibit more precise and accurate portion control, commensurate with manual measurement, such apparatus do not permit the user to instantly preselect the quantity to be dispensed. Of those prior art dispensing apparatus which enable one to vary the quantity of material dispensed, such apparatus cannot be reprogrammed without electrical and/or mechanical adjustment requiring the use of tools.

Another problem or disadvantage attendant in prior art dispensing apparatus is that such apparatus frequently deliver varying portions at given quantity settings, depending upon the head of particulate material stored in the apparatus.

Various prior art apparatus ostensibly intended for use in a home environment have proved to have little value for commercial, or institutional application.

In addition, while some prior art dispensing apparatus may be suitable for dispensing various types of relatively uniform materials, such as granulated sugar, ground coffee, tea, etc., such apparatus have proven unacceptable for dispensing materials composed of a variety of ingredients of substantially varying particle size, such as instant soup mixes, etc. Needless to say that every prior art dispensing apparatus does not exhibit each of the drawbacks as set forth above. However, those prior art apparatus exhibiting the least disadvantages have generally been bulky, complex and expensive and therefore have not come into common use in the home, or portable applications in the outdoor environment, as opposed to commercial or institutional applications.

Accordingly, it is a general object of this invention to provide a dispensing apparatus which overcomes the disadvantages of the prior art.

It is a further object of this invention to provide dispensing apparatus which is effective for dispensing flowable, hygroscopic and other particulate materials.

It is a further object of this invention to provide apparatus for accurately and repeatably dispensing flowable, hygroscopic and other particulate materials.

It is a further object of this invention to provide dispensing apparatus that transfers hygroscopic and other particulate materials from a processor's original container in accurately measured amounts with so little exposure to the ambient atmosphere that supplementary means for creating a dry environment is unnecessary.

It is still a further object of this invention to provide apparatus for dispensing flowable hygroscopic and other particulate materials in readily adjustable quantities.

It is still a further object of this invention to provide apparatus for dispensing flowable hygroscopic and other particulate materials accurately in response to an infinite number of settings within a given dispensing range.

It is still a further object of this invention to provide an apparatus for dispensing flowable hygroscopic and other particulate materials accurately within a multiple of ranges through the simple manual substitution of metering means of varying size, appropriate to a given range.

It is still a further object of this invention to provide apparatus for dispensing flowable, hygroscopic and other particulate materials from containers while maintaining the integrity of the contents of said container between cycles of operation.

It is still a further object of this invention to provide a manually operable apparatus for dispensing flowable, hygroscopic and other particulate materials.

It is yet a further object of this invention to provide apparatus for dispensing flowable hygroscopic particulate materials which apparatus does not destroy the character of the materials during the dispensing operation, yet is suitable for use with materials composed of a variety of ingredients of varying particle size.

It is yet a further object of this invention to provide apparatus for dispensing flowable hygroscopic and other particulate materials, which apparatus operates by gravity, consistently and irrespective of the head of material stored within the apparatus.

It is yet a further object of the invention to provide in an apparatus for dispensing flowable hygroscopic and other particulate material a product contacting portion of which can be disassembled, clean, modified or reassembled manually and without tools or special techniques.

These and other objects of the instant invention are achieved by providing apparatus for repeatedly dispensing flowable, hygroscopic and other particulate materials from a container in measured quantities while isolating the remainder of material within the container from the ambient atmosphere. The apparatus comprises a funnel unit having a side wall which tapers downward from an inlet to an outlet. The container is disposed above the inlet. Flow control means are provided interposed between the container and the inlet of the funnel unit. Hollow metering means, having a peripheral free edge, is disposed within the funnel unit adjacent to the outlet. The metering means is mounted for reciprocation between a charging position in which the peripheral free edge of the metering means is spaced a predetermined distance above the side wall of the funnel unit and a closed position in which its peripheral free edge contacts the tapered side wall of the funnel assembly adjacent to the outlet thereof to form a dispensing chamber.

When the metering means is in the charging position, particulate material is enabled to flow into the portion of the funnel unit adjacent the outlet until it reaches its angle of repose. When the metering means is in the closed position, after being in the charging position, a predetermined portion of material is trapped in the dispensing chamber. The outlet includes a selectively operable, moveable closure plunger for opening the outlet when the metering means is in the closed position to enable materials trapped within the dispensing chamber to drop through the outlet. The closure plunger keeps the outlet closed at all times until operated after the metering means is in the closed position, to preclude the ambient atmosphere from entering the container.

In accordance with one aspect of this invention, the height of the metering means in the charging position is adjustable to establish the quantity of material to be dispensed.

Other objects and many of the attendant advantages of this invention will be readily appreciated as the same becomes better understood by reference to the following detailed description when considered in connection with the accompanying drawing wherein.

Figures 1, 2:
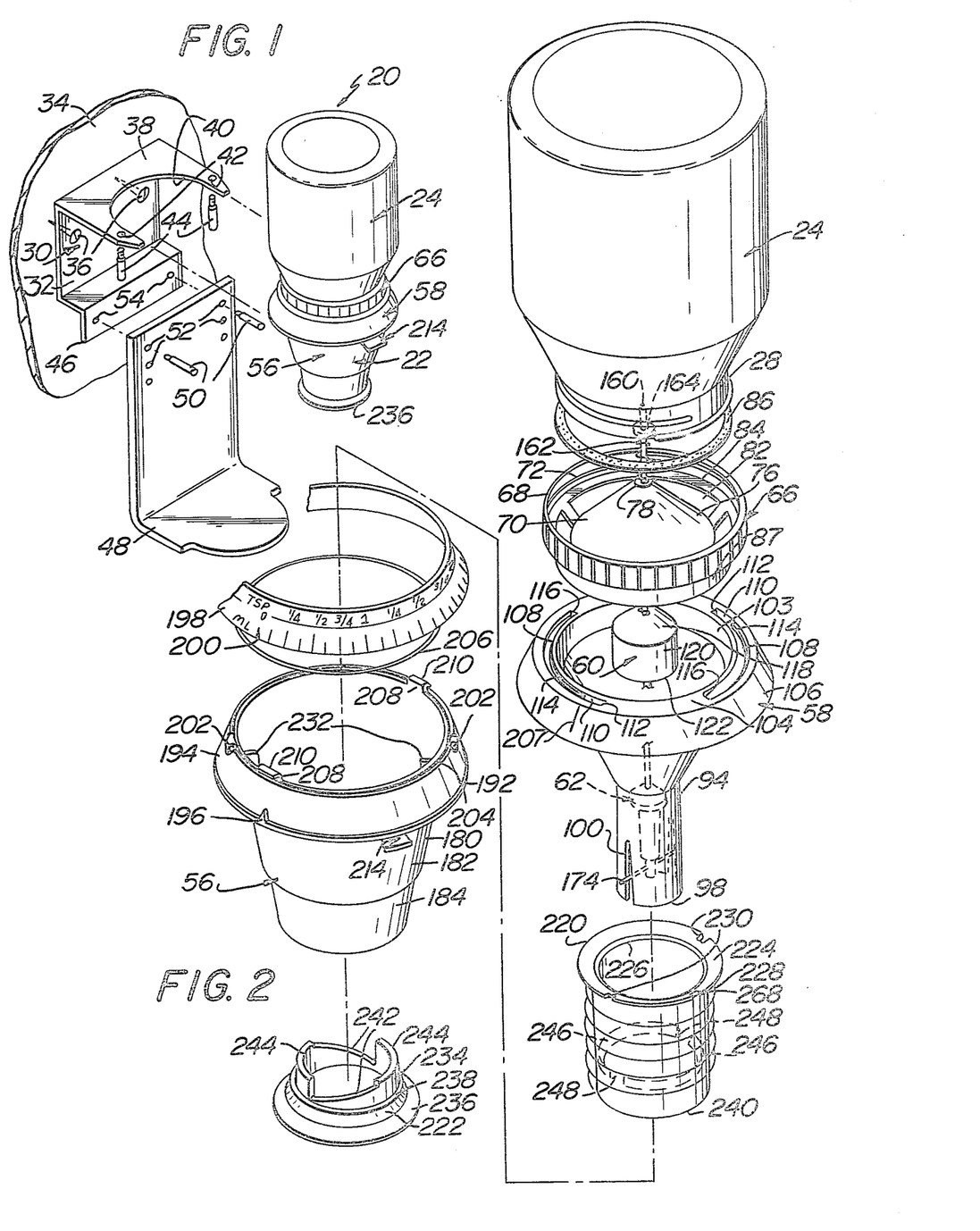
FIG. 1 is a partially exploded perspective view of the dispensing apparatus of the instant invention.
FIG. 2 is an enlarged, partially exploded perspective view of a portion of the apparatus shown in FIG. 1.

Referring now in greater detail to the various figures in the drawings, wherein like reference characters refer to like parts, a dispensing apparatus in accordance with the instant invention is shown at 20 in FIG. 1. The apparatus 20 is arranged to dispense flowable particulate materials and, more particularly, hygroscopic particulate materials such as spray-dried and freeze-dried instant coffees, tea, soup mix, cold drink mix etc., in precisely measured quantities, while maintaining the integrity of said material by isolating it from the ambient atmosphere.

The apparatus basically consists of dispensing unit 22 which is a two part device. The first, part which will be described in detail later, includes a funnel and metering unit, and is arranged in the preferred embodiment to utilize the container in which the particular product is sold as the storage means. The second part of the apparatus is in the form of a mounted receiver housing assembly which will be described in detail later and when coupled to the funnel and metering unit during the dispensing cyhcle exposes the product stored in the apparatus to only that small volume of air which displaces the quantity dispensed during each dispensing operation.

The dispensing unit of the instant invention can be used with various conventional type merchandizing containers, e.g., 70 mm wide mouth, screw thread jars, four (4) inch (10 mm) cans, bowl seal jars like that sold by Anchor Hocking Glass Corp., etc., by the selection of a suitable adapter (to be described later) to accomodate the particular container's mouth.

In the embodiment of FIGS. 1-9, the container shown is a 70 mm wide mouth jar 24. The lid of the jar is unscrewed, the food processor's protective vapor seal removed and the jar with its contents 26 (FIG. 5) is secured to the funnel portion of the dispensing unit 22 by inverting the funnel with a suitable configured adapter welded thereto, and affixing it to the jar mouth 28.

The assembled funnel and jar are then inverted allowing the contents of the jar to fall into the funnel and the assembly is inserted into the receiver housing assembly to ready the completed dispenser unit 22 for use.

While the apparatus must be oriented so that the product container is disposed above the dispensing unit, the apparatus itself may be disposed in various ways, e.g., within a housing adapted for disposition on a horizontal surface, like a counter top etc. In the embodiment shown in FIG. 1 the apparatus 20 is shown mounted on a wall or bulkhead 34 by a bracket assembly 30 (FIG. 1). The assembly 30 includes a mounting plate 32 which abuts the wall and is secured thereto via screws 36. The top of the mounting plate in the form of horizontal flange 38 having a semicircular recess 40 in the front edge thereof configured to receive the dispensing unit's housing (to be described later). A pair of holes 42 are located in the flange 38 on each side of the recess for receipt of a pair of threaded mounting fasteners 44 which extend into the dispensing unit's housing to hold it in place. The lower portion of the mounting plate includes a vertical flange 46 on which an L-shaped shelf 48 is mounted, via a pair of threaded fasteners 50. The shelf serves as the support for a cup or other vessel into which the particulate material is to be dispensed. The back portion of the shelf includes plural horizontally disposed pairs of mounting holes 52. By the insertion of the fasteners 50 through any selected pair of holes 52 and into an aligned pair of threaded holes 54 in the flange 46 the spacing between the bottom of the dispensing unit 22 and the base of the shelf 48 can be adjusted to accomodate various size receiving vessels.

Figure 5:
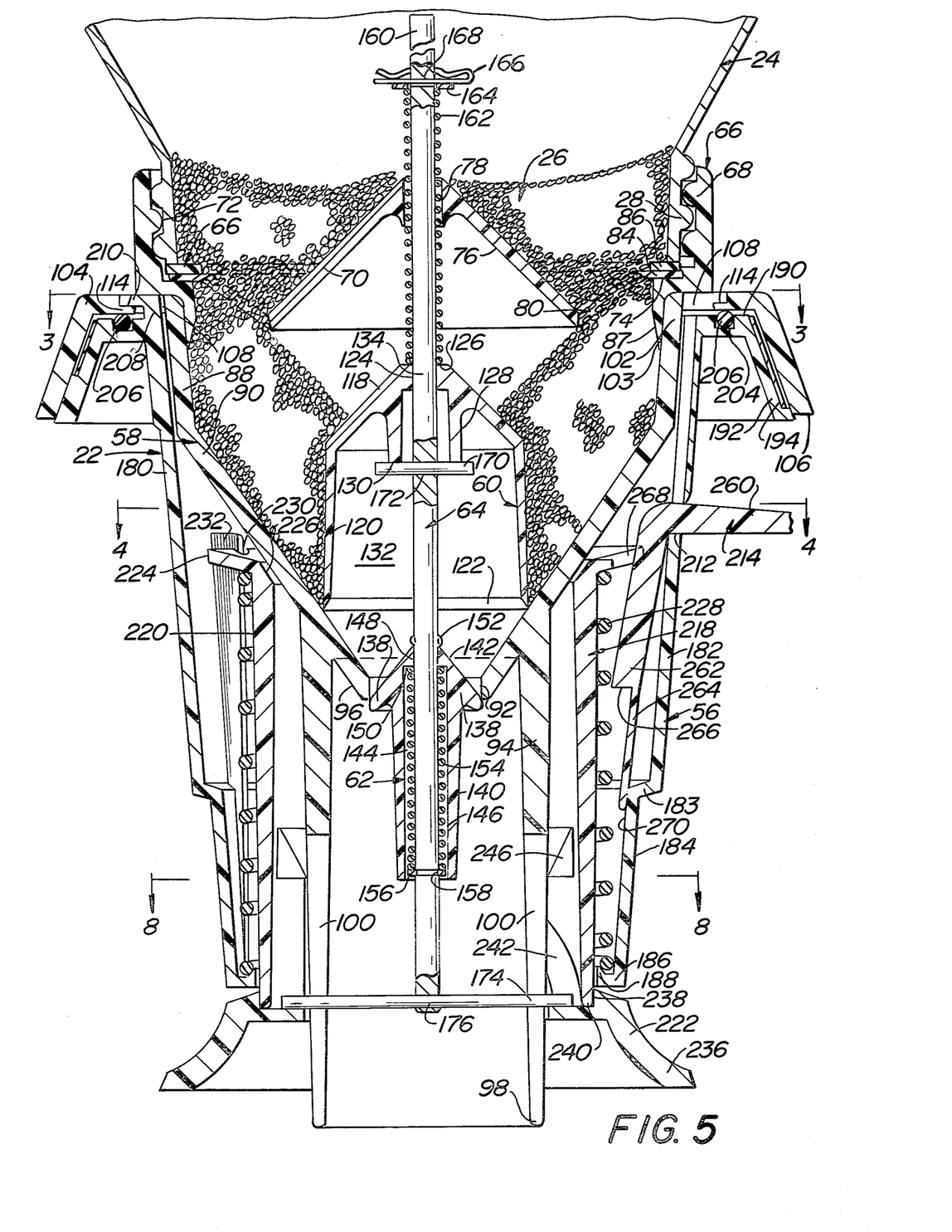
FIG. 5 is an enlarged sectional view of the apparatus shown in FIG. 1 illustrating the apparatus prior to a dispensing operation.

As seen in FIG. 5, the dispensing unit 22 basically comprises a receiver housing assembly 56 in which there is disposed a funnel unit 58 adapted for receipt of particulate material from the jar 24 and having an outlet, metering means 60 located within the funnel unit for trapping a predetermined quantity of material in a dispensing chamber formed between it and the bottom of the funnel unit, a closure means 62 for selectively opening and closing the funnel unit's outlet to permit material trapped within the dispensing chamber to drop out of the unit and to close the funnel assembly at all other times, an actuator assembly 64 coupled to the metering means 60 and the closure means 62 for establishing the quantity of material trapped within the dispensing chamber, for operating the metering means and for operating the closure means and a flow control-adapter assembly 66 for securing the jar 24 to the dispenser unit and controlling the flow of particulate material from the jar to the funnel assembly, irrespective of the head of material in the jar.

The flow control-adapter assembly 66 comprises an adapter ring 68 and a flow control disc 70. The ring 68 has a threaded inner wall 72 for receipt and engagement with the threads on the mouth 28 of the jar 24. The bottom of the inner wall 72 terminates in an inwardly extending horizontal ledge portion 74. The flow control disc 70 includes a central conically shaped walled portion 76 which slopes downward from its apex. The apex includes an opening 78 through which a portion of the actuator assembly 64 passes. The central walled portion 76 of the flow control disc terminates at its bottom edge in a flange 80, which extends upward at an acute angle thereto. A plurality of arcuate slots 82 (FIGS. 2 and 3) are cut in flange 80. The peripheral edge 84 of the flanges 80 extends horizontally and is disposed on the ledge 74 of the adapter ring 68. A flat sealing gasket 86 is disposed on the horizontal flange portion 84. The gasket and underlying flange portion are tightly engaged between the jar's mouth and the adapter ring's ledge when the jar is screwed into the adapter. This action seals the interior of the jar from the ambient atmosphere, while also securing the flow control disc in place.

As can be seen in FIG. 5, the bottom of the adapter ring 68 includes a downwardly projecting cylindrical side wall 87, whose outer surface tapers inward gradually and whose inner surface tapers outward. The funnel unit 58 is shown clearly in FIG. 2 and basically comprises a funnel shaped portion having an upper side wall section 88 which gradually tapers downward and merges into a lower side wall section 90. The lower section tapers at a 55° angle to the vertical axis. The lowermost portion of the lower side wall section 90 includes a central opening or outlet 92. A tubular extension or neck 94 projects downward from the underside 96 of the inner wall section 90 and encircles the outlet 92. As seen in FIGS. 2 and 5, the end 98 of the funnel neck 94 includes a pair of vertical guide slots 100 cut therein diametrically opposed to each other. The slots 100 are adapted for receipt of a cam follower means of the actuator assembly. The cam follower means as will be described in detail later coacts with cam means in the housing to adjust the quantity of material being dispensed.

As can be seen in FIG. 2, the top 102 of the upper section 88 of the funnel unit is in the form of a horizontally extending flange 104. The peripheral free edge of the flange 104 extends downward in an acute angle to form a lip 106. The mouth of the funnel, denoted by the reference numeral 103, is configured to receive the downwardly extending side wall 87 of the adapter ring. The ring is frictionally fit and welded therein to firmly secure the adapter ring 68 to the funnel unit 58.

The horizontal flange portion 104 of the funnel unit includes a diametrically opposed pair of arcuate locking slots 108. The slots are of the same radius and each includes an enlarged entrance or clearance portion 110 contiguous with the front edge 112 of the slot and a peripheral edge 114 of lesser thickness than the thickness of the flange portion 104 and extending into the slot along the outside edge thereof from the enlarged clearance portion 110 rearward to the back edge 116 of the slot.

As will be described in detail later, the slots 108 coact with locking lugs, forming a part of the receiver housing assembly 56, to secure the funnel unit within the housing assembly, while permitting the funnel unit to be rotated about the vertical axis. As will be described in detail later, it is the rotation of the funnel unit within the housing which causes the cam follower to coact with the cam means to establish the quantity of material to be dispensed during the dispensing operation.

The metering means 60 is in the form of a bell-shaped member having a conical top section 118 and a gradually flared lower section 120. The peripheral edge 122 of the lower section 120 is bevelled to form a knife-like edge. A hole or opening 124 extends through the apex of the top section of the metering ball. The uppermost portion of the top section contiguous with the opening 124 and referred to by the reference numeral 126 is flat. A tubular projection 128 extends downward on the inside of the metering bell and is concentric with the opening 124. The bottom surface 130 of the tubular projection is flat and forms a stop surface (to be described later).

The metering bell is arranged to be reciprocated by the actuator assembly 64 between a closed position (shown in FIG. 5) wherein the peripheral edge 122 of the bell abuts the inner surface of the lower section 90 of the funnel unit and a charging position wherein the peripheral edge is disposed a predetermined and adjustable distance thereabove. In the closed position the metering bell encloses the portion of the funnel contiguous with the outlet 92 to form a dispensing chamber 132. The dispensing chamber fills with a predetermined quantity of particulate material, depending upon the height of the metering bell in the charged position. In that regard, when the metering bell is moved to some charging position, e.g., like that shown in FIG. 6, above the inner surface of the funnel unit, particulate material 26 is enabled to flow from the jar 24 under the influence of gravity through the slots 82 in the flow control disc 70 and into the mouth 103 of the funnel unit. The material flows through the space between the peripheral edge 122 of the metering bell and the inside surface of the funnel unit to the space about the outlet 92. The material fills that space until the material reaches its "angle of repose". As is known, the "angle of repose" is the maximum slope which particulate material will stand without sliding on itself and is a constant value, within close tolerances, for each type of particulate material. Accordingly, each time that the metering bell is raised to the same vertical position above the funnel unit, thereby creating an identically sized passageway through which the material can flow, the same quantity of material will reach the bottom of the lower section of the funnel unit adjacent its outlet. When the metering bell is thereafter moved to the closed position, its knife-like peripheral edge 122 cuts through the material disposed adjacent to the outlet to trap a precise quantity of material within the dispensing chamber 132.

As noted briefly heretofore, the dispensing unit includes cam means within the receiver housing assembly 56 which cooperate with the actuator assembly to adjust the height the metering bell 60 in its charging position to thereby control the angle of repose of the material and hence adjust the quantity of material being dispensed. In addition, as will be described later the actuator assembly is arranged to raise the metering bell 60 to the exact same charging position as in the immediately preceding dispensing operation, unless adjusted otherwise. This feature ensures that one can repeatedly dispense a predetermined quantity, e.g., a teaspoon, of material, without necessitating the resetting or adjustment of the unit.

Figure 6:
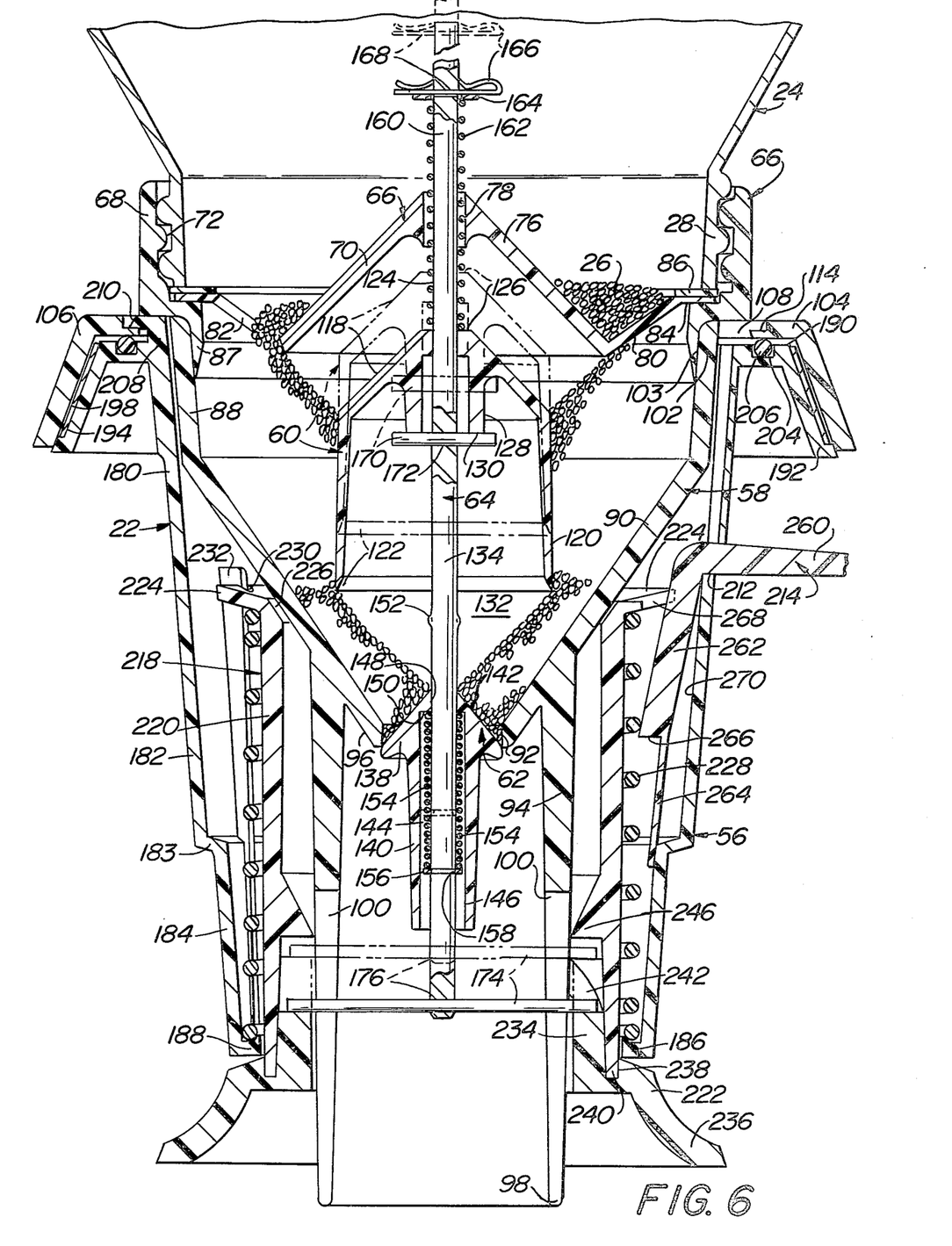
FIG. 6 is a sectional view, similar to that of FIG. 5, showing the apparatus as it measures out a quantity of material for dispensing.

The maximum height that the metering bell can be set to is shown in phantom lines in FIG. 6.

The actuator assembly 64 is best seen in FIG. 5 and comprises an elongated actuator rod 134 which extends vertically through the funnel unit 58, the flow control-adapter assembly 66 and into the mouth of the connected jar 24. The metering bell 60 and the closure 62 are mounted on the actuator rod 134. The actual description of the features and operation of the actuator assembly 64 will be set forth in detail later. Sufficient for now to say that the actuator rod 134 of the actuator assembly is arranged to be reciprocated up and down between the charging position and a position below the closed position and hereinafter referred to as a release position, to operate the metering means 60 and the closure means 62. To that end the upward movement of the actuator rod carries the metering bell 60 up from contact with the funnel unit, i.e., the closed position, to the predetermined higher elevation of the charging position. The amount of upward travel of the actuator rod to establish the charging position of the metering bell is adjustable and is set by the cam means which will be described in detail later.

The plunger 62 is mounted for relative movement with regard to the actuator rod 134 such that the closure 62 remains seated within the outlet 92 as the metering bell 60 is carried upward from the closed position to the charging position and vice versa. This action precludes the premature dispensing of particulate material from the unit while also acting as a seal against the ingress of ambient atmosphere into the unit. Further downward movement of the actuator rod 134 down to the release position causes the closure 62 to move out of the outlet 92, whereupon the particulate material within the dispensing chamber is released and dropped out of the outlet for receipt by a cup (not shown) or other vessel disposed on the shelf 48 beneath the dispensing unit 22.

The metering means, like the closure means, is mounted for relative movement with respect to the actuator rod 134 such that the metering means remains in its closed position as the closure means is carried from the outlet to the release position and vice versa. This action precludes premature filling of the dispensing chamber 132, i.e., until the closure is reseated within the outlet 92.

As will be described in detail later, latch means are provided within the receiver housing to pacify its several functions including the raising of the metering means when the funnel unit is rotated about its axis as a preface to filling the dispensing chamber 132, at any particular setting. The effect of receiver pacification is that the closure means 62 remains in its normally closed position in the funnel outlet 92, and the metering means 60 remains in its normally closed position within the funnel as a result of the bias produced by springs, to be described in detail later, forming a part of the actuator assembly. This action sustains the funnel unit's double seal against the ingress of humidity.

The closure means is best seen in FIG. 5 and comprises a cylindrical plunger 62 having an enlarged cap portion 138 of slightly larger outside diameter than the diameter of the outlet 92 and an elongated shaft portion 140. The top surface 142 of the cap 138 is conical. The plunger includes a central passageway 144 through which the actuator rod 134 passes. The passageway 144 includes a large diameter bottom bore 146 and a smaller diameter top bore 148. The interface of the bores 146 and 148 forms a ledge 150. A plurality of small nibs or projections 152 are swaged on the actuator rod at an intermediate portion thereon and extend outward beyond the radius of the top bore 148. The nibs 152 preclude the plunger 62 from moving up the actuator rod past the nibs. A helical compression spring 154 is disposed within the lower bore 146 and around the actuator rod. The spring is held in place between the ledge 150 and a retaining ring 156 mounted within an annular recess 158 in the rod.

The upper portion 160 of the actuator rod extends through the opening 78 in the flow control disc 70. A helical compression spring 162 is disposed around the rod portion 160 and also extends through the opening 78. The spring 162 is interposed between the planar top 126 of the metering bell 60 and a stop washer 164. The washer 164 is releasably secured to the actuator rod by a cotter pin 166 which is in turn releasably secured in a hole 168 extending through the rod. The releasable securement of the cotter pin and washer is important to facilitate hand disassembly, cleaning and the substitution of metering bells of different diameters to accomodate different ranges of material measurement.

A carrier pin 170 extends through an opening 172 in an intermediate portion of the actuator rod 134 and above the nibs 152. A cam follower in the form of an elongated pin 174 extends through an opening 176 at the bottommost end of the actuator rod. Each end of the pin 174 extends through an associated vertical guide slot 100 in the funnel neck 94 of the funnel unit.

As will be appreciated by those skilled in the art, as the actuator rod is carried down to the release position from the point at which the metering bell 60 makes contact with the funnel unit, i.e., the closed position, the nibs 152 on the actuator rod make contact with the top of the closure plunger 62 contiguous with the bore 148 to carry the plunger downward. The compression spring 162 takes up the downward travel of the actuator rod as it moves to the release position since the peripheral edge 122 of the metering bell is in contact with the funnel and cannot be carried any lower by the downward movement of the actuator rod. In addition, the compression spring 162 provides a sufficient downward force onto the metering bell to insure that its peripheral edge 122 makes good contact with the funnel unit when the metering bell is in the closed position, thereby ensuring proper isolation of the metered quantity of material in the dispensing chamber, while precluding ingress of moisture into the dispensing unit.

Upward movement of the actuator rod causes the carrier pin 170 to push upon the end surface 130 of the tubular projection 128 within the metering bell to carry the bell upward to its charging position. The compression spring 154 within the closure plunger 62 compresses on the upward travel of the actuator rod as it moves the metering means from the closed position to the charging position. In addition, the spring 154 provides an ever increasing upward force on the ledge 150 of the plunger to insure that the conical surface 142 of the cap of the plunger makes good contact with the periphery of the outlet 92 of the funnel at all times, except when the actuator rod is in the release position, thereby providing an additional seal against the ingress of moisture into the dispensing unit.

The receiver housing assembly 56 basically comprises a housing shell 180 of generally conical shape having an upper side wall section 182 which joins flange section 183 extending at a slight acute angle to the horizontal, where it joins a lower side wall section 184. The bottom of the lower side wall section includes a peripheral ledge 186 projecting inward and terminating in an upstanding lip 188. The top of the upper side wall section 182 is in the form of a horizontally extending flange 190 terminating in a lip 192 extending downward at an acute angle thereto. A shallow depth, annular recess 194 is cut into the upper surface of the lip 192 and extends for a substantial portion of the width thereof except for the outermost edge. A triangular projection 196 (FIG. 2) is located within the shallow recess 194 contiguous with the edge of the lip 192. An indicia-bearing band 198 (FIG. 2) in the form of a truncated conical ring is located within the recess 194. The band includes a notch 200 in its lower edge corresponding in size and shape to the triangular projection 196 to correctly position the band within the recess. The band includes plural indicia along its top and bottom edges for indicating the quantity of material being dispensed at any particular setting. To that end as can be seen in FIG. 2, the upper portion of the band includes a graduated scale in fractions of teaspoons, while the lower section include a scale graduated in milliliters. The notch 200 is aligned with the zero setting of both the scales of the band 198.

A pair of mounting holes 202 extend vertically downward through the horizontal flange portion 190 of the shell. The holes 202 are arranged to receive threaded inserts 203, which accomodate the threaded fasteners 44 therethrough to secure the housing to the bracket 30, via holes 42 therein.

As can be seen in FIGS. 2 and 5, a circular annular groove 204 is cut into the top surface of the horizontal flange 190 of the housing. A resilient O-ring 206 is located within the groove.

The housing shell 180 is configured to receive the funnel unit 58 therein, with the horizontal flange 104 and the angularly extending lip 106 of the funnel unit just overlying the corresponding flange 190 and lip 192 of the housing shell and with the O-ring 206 interposed snugly between flanges 104 and 190.

As noted earlier, the funnel unit is disposed within the housing shell and is arranged to be rotated with respect thereto about the axis of the actuator rod 134. This action establishes the height of metering ball 60 in the charging position, with the greater counterclockwise rotation of the funnel unit effecting a greater raising of the metering bell up to the maximum height shown by phantom lines in FIG. 6.

The O-ring 206, is snugly interposed between the flange 104 and the flange 190 yet nevertheless acts as a slip clutch to permit the funnel unit 58 to be rotated with respect to the shell while also serving as a seal against the ingress of moisture to the interior of the housing.

Figures 3, 4:
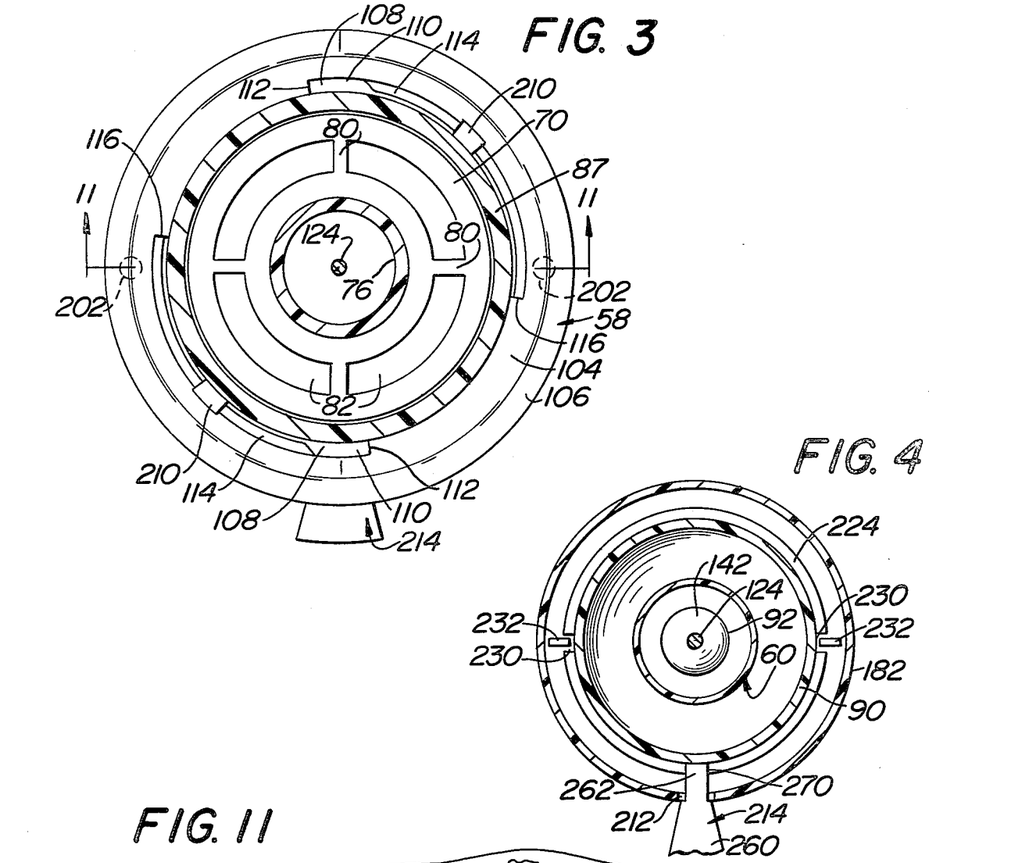
FIG. 3 is a sectional view taken along line 3—3 of FIG. 5.
FIG. 4 is a reduced sectional view taken along line 4—4 of FIG. 5.

A pair of locking lugs 208 project upward from the top surface of the horizontal flange 190. Each lug includes a horizontal locking tab 210 at the top thereof. Each lug is arranged to extend through an associated enlarged entrance portion 110 of the arcuate slot 108 in the horizontal flange 104 of the funnel unit. When the funnel unit is rotated counterclockwise with regard to the housing shell, to thereby establish the quantity setting for the materials to be dispensed, the lugs slide down the slots 108 from the entrance portion such that each of their horizontal tabs 210 overlies the ledge portion 114 of the slots 108, thereby locking the funnel unit to the housing. In FIG. 3 there is shown the funnel unit rotated approximately 45° counterclockwise to lock the funnel unit to the housing and to establish the setting for a quantity of material to be dispensed.

In accordance with a preferred aspect of this invention, the entire funnel unit is formed of a transparent plastic such that the scales on the band 198 can be read through the downwardly extending lip 106. To that end the angularly extending lip 106 includes an indicator line 207 etched thereon and aligned with the enlarged entrance 110 of one slot 108. The line 207 serves as the pointer for the scales of the band 198 to indicate the quantity of the material to be dispensed by operation of the unit at that setting. In this regard, when the funnel unit is disposed within the housing shell with its locking tabs 210 extending into the enlarged entrance portion 110 of the slots, the marker line 207 directly overlies the projection 196 and hence the zero (0) mark on the scales of the band 198. The counterclockwise rotation of the funnel unit which causes the metering bell to rise to establish the quantity of material to be dispensed, causes the line 207 to move to the position over the scales of the band 198 which indicates the quantity of material to be dispensed at that setting.

An opening 212 is provided within the upper side wall section 182 of the housing shell and located on the front thereof when the housing is mounted on the support bracket. The opening 212 is provided to receive a portion of a trigger 214 (to be described in detail later) which, until actuated, keeps the metering bell and the closure plunger in contact with the funnel unit so as to provide two seals against the ingress of ambient moisture into the jar 24.

A sleeve-cam assembly 218 is also mounted within the housing shell. The assembly 218 comprises a sleeve element 220 and a cam element 222. The sleeve 220 is a cylindrical member through which the tubular extension 94 of the funnel unit extends. The upper end of the sleeve 220 includes a flange 224. The flange extends at a slight acute angle to horizontal. The mouth of the sleeve, denoted by the reference numeral 226 tapers downward to accommodate the under surface of the funnel unit. A helical compression spring 228 is disposed about the sleeve 220 and is interposed between the ledge 186 of the housing shell and the underside of the flange 224. A pair of diametrically opposed slots 230 are provided in the periphery of the flange 224. The slots coact with means, to be described hereinafter, in the housing shell to guide the sleeve for vertical movement while precluding rotation of the sleeve about the axis of the actuator rod 134. To that end, as can be seen in FIGS. 2, 4 and 5, the interior of the housing shell includes a pair of fins 232. The fins are aligned with the housing mounting holes 202 and each fin projects radially inward. Each fin extends from the lower edge of the housing shell to approximately the height of the opening 212 for the trigger 214. Each fin is arranged to be received within an associated slot 230 in the flange of the sleeve 220.

Figure 2A:
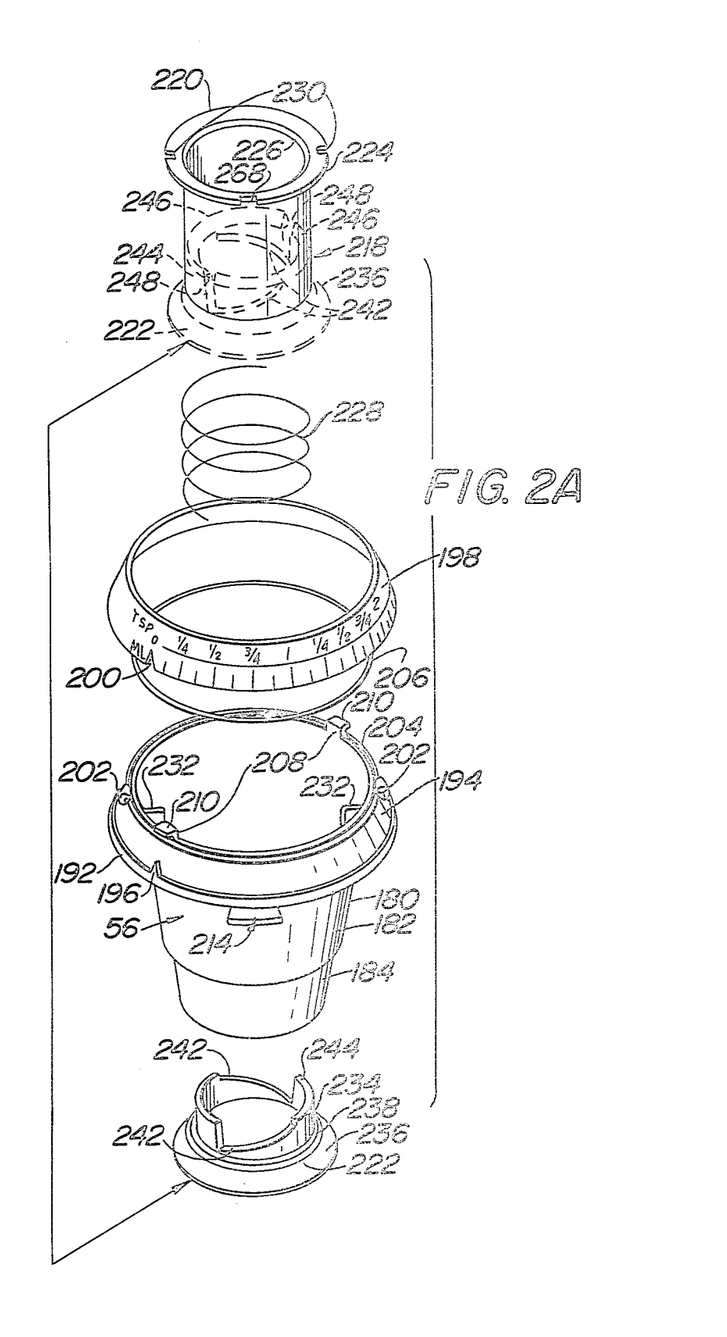
FIG. 2A is another enlarged partially exploded perspective view of the portion of the apparatus shown in FIG. 2.
Figures 8, 9:
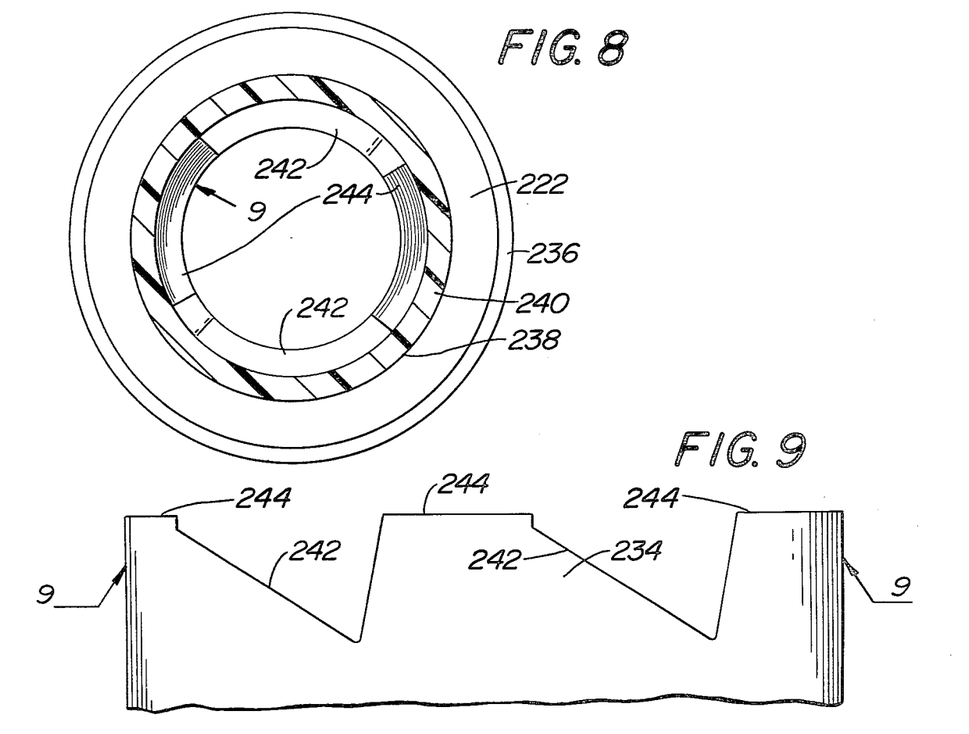
FIG. 8 is a sectional view taken along the line 8—8 of FIG. 5.
FIG. 9 is a side view of a portion of the apparatus shown in FIG. 8, but laid flat.

The cam element 222 is best seen in FIGS. 2A, 8 and 9. As can be seen therein the element 222 is a ring like member having an upwardly projecting cylindrical side wall 234 with a skirt section 236 projecting outward from the bottom thereof. An annular channel extends around the side wall at the interface of the skirt 236 and the bottom section of the side wall 234. The channel 238 is arranged to receive and frictionally hold therein the free edge 240 of the bottom of the sleeve element 220. A key projection (not shown) is located within the channel 238 and is adapted to be received within a key slot (not shown) in the bottom edge 240 of the sleeve 220 to precisely align the cam element 222 with the sleeve element 220 to form the sleeve-cam assembly 218.

As can be seen in FIGS. 2, 8 and 9, the side wall section 234 of the cam element 222 includes a pair of cam tracks 242. The cam tracks 242 are ramp-like surfaces extending from a bottom of channel 238 up into approximately the top edge 244 of the side wall 234. Each cam surface 242 extends for approximately 90° about the periphery of the cylindrical side wall 234. In FIG. 9 there is shown the cylindrical side wall 234 laid flat to show the shape of the cam surfaces 242. As can be seen in FIG. 2A, the lowermost portion of each of the cam surfaces 242 are diametrically opposed, as are the uppermost points of the cam surfaces.

As can be seen in FIGS. 2 and 5, the interior surface of the sleeve element 220 includes a dump ring which is in the form of a projection 246. The dump ring 246 extends about the inner circumference of the sleeve 220 except for two opposed vertical slots 248. The upper surface of the projection 246 tapers downward in an inward radial direction. The ring 246, as will be described in detail later, cooperates with the actuator assembly to move the plunger from the funnel outlet to effect the dispensing of particulate materials from the dispensing chamber. When the sleeve element 220 and the cam element 222 are secured together, the top surface 244 of the side wall 234 in the cam element just underlies the bottom of the ring 246, with each slot 248 being located directly over the lowermost portion of a respective cam track 242. The ring 246, as will be described in detail later, coacts with the actuator assembly to effect the removal of the closure from the outlet. The sloped surface of the dump ring acts as a particle deflector to deflect random material which may get into the sleeve through the funnel slots 100.

Figure 7:
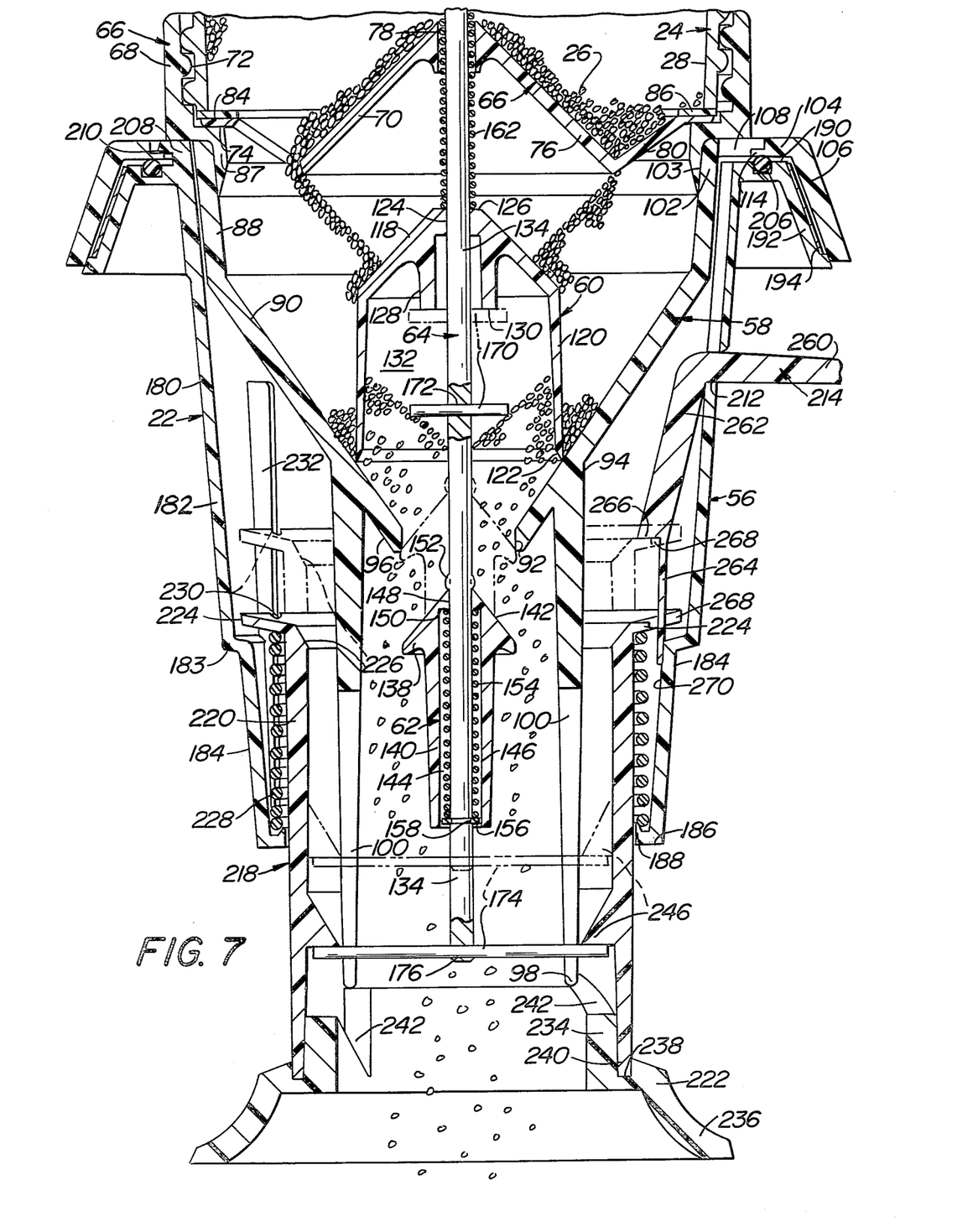
FIG. 7 is a sectional view, similar to that of FIG. 6, but showing the apparatus dispensing the measured quantity of particulate material.

As can be seen in FIG. 7, the trigger 214 is an angularly shaped member which is preferably formed as an integral unit of a highly resilient material such as DELRIN. The trigger basically comprises an actuating lever section 260 which extends through the opening 212 in the housing shell, a latching section 262 extending through the opening and downard at an acute angle to the actuating lever and an elogated spring finger 264 extending vertically downward from the end 266 of the latching section. It should be noted that the flexibility of the spring finger 264 is such that the trigger may be removed and, if necessary, reinstalled, depending on the dispenser application.

As can be seen in FIGS. 2 and 7, the flange 224 of the sleeve-cam assembly includes a radially extending notch 268 in its periphery. The notch is located halfway between the two slots 230 such that it is axially aligned with the latching section 262 of the trigger. The depth of the notch 268 is less than the width of the flange 224 and the depth of the end 266 of the latching section of the trigger. When the trigger is free, that is not operated by the user, its finger 264 makes contact with the inside wall 270 of the lower section 184 of the housing to cause the end 266 of the latching section to extend inward and overlying the flange portion contiguous with the bottom of the notch 268. Accordingly, the end of the latching section 266 acts as a stop preventing the upward travel of the sleeve beyond the height of the trigger as shown by the phantom lines in FIG. 7.

The assembly of the dispensing unit 22 is as follows:

The housing shell 180 and the sleeve-cam assembly 218 are assembled by first inserting the latching section 262 of the trigger 214 through the opening 212 in the housing shell 180. The latching section passes through the opening 212 and extends downward at an acute angle to the actuating lever, with its elongated spring finger 264 extending vertically downward so that the tip of the finger rests against the inside wall 270 of the lower section 184 of the housing shell 180.

The sleeve-cam assembly 218 is assembled within the housing shell 180 by seating the compression spring 228 on the ledge 186 in the lower housing shell. The sleeve 220 is then inserted in the spring and housing shell such that each of the sleeve slots 230 receives a respective guide fin 232, and the radially extending trigger notch 268 receives the trigger latching section 262 of the installed trigger 214. The cam element 222 is then secured to the sleeve element 220 by aligning the key slot in the free end 240 of the sleeve element, with the complimentary key projection within the circular channel 238 in the cam element and then welding the two components together. The indicia-bearing band 198 is fitted to the housing shell 180 so that its notch 200 fits the pointer 196 and thereby properly locating the band in recess 194 of the housing shell. The O-ring 206 is inserted in the annular groove 204 of the flange 190 of the housing shell.

The funnel 58 incorporating the actuator assembly 64 with the metering bell 60, and closure plunger 62 mounted thereon, are so disposed on the actuator rod 134 within the funnel that the metering bell and the closure plunger are held closed within the funnel as heretofore described by the diametrically opposed bias of their springs on the actuator assembly 64, thereby creating a double seal against the ingress of ambient atmosphere once the assembled funnel unit is secured to the jar 24.

To complete the assembly of the dispensing unit 22, the jar 24 and assembled funnel unit are inserted in the mounted receiver housing assembly 56 so that the indicator 207 of the funnel unit 58 is essentially in line with the pointer 196, and hence, the zero (0) mark on the indicia-bearing band 198. As the assembled funnel unit progressively enters the receiver housing assembly 56, the opposed ends of cam follower pin 174, which extend out of the vertical slots 100 of the funnel neck 94, pass through the dump slots 248 of the dump ring 246 to the bottom of the cam tracks 242, simultaneously allowing the locking tabs 210 of the housing shell 180 to extend through the enlarged entrance portions 110 of slots 108 of the assembled funnel as shown in FIG. 5.

Provided the sleeve-cam assembly 218 is not secured in the latched position by trigger 214, the rotation of the funnel unit 58 counterclockwise about its longitudinal axis to lock the funnel unit to the housing shell 180 causes the ends of the cam follower pin 174 to ride up the ramp-like cam tracks 242. This action causes the actuator rod 134 to rise vertically within the funnel. The more the funnel unit is rotated counterclockwise with respect to the housing, the greater the upward travel of the actuator rod.

Operation of the dispensing unit 22 described heretofore is as follows:

The particulate material 26 flows through the slots 82 in the flow control disc 70 into the mouth of the funnel unit 58 and around the metering bell 60 as shown in FIG. 5. At this time the metering bell is in the closed position such that the material is isolated from the dispensing chamber 132 and thus the outlet 92. As will be appreciated by those skilled in the art, the flow control disc 70 intercepts the random weight of material 26 within the jar 24 in such a manner as to create, what can be called, a secondary reservoir of constant weight material about the metering bell 60, irrespective of the changing level and weight of material in the jar. This stable weight of flowable, dry, particulate material about the metering bell insures the accuracy and repeatability of the operation of the dispensing unit 22.

The funnel unit 58 is rotated counterclockwise (in the view shown in FIG. 3) to raise the metering bell from the position shown in FIG. 5 to an elevation above the bottom of the funnel unit, i.e., the charging position. In FIG. 6 the metering bell 60 is shown in full at one exemplary charging position elevation. As mentioned earlier, the rotation of the funnel unit about its longitudinal axis with respect to the housing causes the actuator rod to be raised vertically. This action causes the carrier pin 170 to make contact with the underside surface 130 of the metering bell to carry the bell upward with the actuator rod 134. When the funnel unit has been rotated to the appropriate rotational position to dispense a desired quantity of material, its position is indicated by the marker line 207 on the funnel unit lip 106 overlying the associated scale marking on the band 198.

The raising of the metering bell 60 to the charging position enables the particulate material within the secondary reservoir, i.e., surrounding the bell, to flow around the bell between its peripheral edge 122 and the underlying surface 90 of the funnel unit to fill the space above the outlet 92 to the angle of repose of the material. Since the pressure of the material about the metering bell is maintained constant by virtue of the action of the flow control disc 70, the raising of the bell precisely the same amount of each dispensing cycle allows precisely the same amount on material to flow at precisely the same rate into the bottom of the funnel unit and under the metering bell.

The height setting of the metering bell when the cam follower pin is at the top of the cam surface 242 is shown by the phantom line in FIG. 6 and is referred to as the maximum charging position. When the metering bell is at the maximum charging position the dispensing unit is set to dispense the maximum quantity of material for that size metering bell. It should be pointed out at this juncture that the apparatus 20 of the instant invention can be utilized to dispense greater or lesser quantities of material by the mere substitution of a larger or smaller sized metering bell for that shown in the drawings herein. For example, in order to dispense tablespoon size quantities, a larger diameter bell would be used and a corresponding indicator band 198 would be used for those components shown herein.

The spring 228 disposed about the sleeve 220 is sufficiently preloaded to overcome the combined weights of the material 26 being measured, the plunger 62, the actuator assembly 64, the sleeve and cam assembly 218, the metering bell spring 162, and the load of the plunger closure spring 144 up to and including the load experienced when the metering bell is at the maximum charging position.

It should be pointed out at this juncture that when the metering bell is carried upward from the closed position to any charging position, its flared side wall section disturbs the surrounding particulate material 26 such that the material flows more readily around and under the bell to fill the space above the outlet of the funnel unit. The extending cotter pin 166 mounted at the top of the actuator rod and within the jar 24 performs a similar function on the material within the jar.

Once the metering means has been raised to a predetermined charging setting, the apparatus is then in condition to actually meter out such quantity of material and thereafter dispense it. The metering action and the dispensing action are effected by the downward movement of the actuator assembly under the control of the user.

The downward movement, or downstroke, of the the actuator assembly 64 to which the metering bell 60 is coupled is accomplished by pulling down on the flared skirt 236 of the sleeve-cam assembly 218, thereby overcoming the load on the sleeve-cam spring 228. This action in turn allows the closure plunger spring 154, which is under compression, and coupled to the actuator assembly, to cause the metering bell to move downward until it reaches the closed position, wherein its peripheral edge 122 makes contact with the inside surface 90 of the funnel unit like that shown in FIG. 7. The sharp edge of the metering bell facilitates the movement of the bell through the underlying material 26 and into contact with the funnel unit.

Continued downward movement of the cam-sleeve assembly causes the underside surface of the dump ring 246 to abut the ends of the cam follower pin 174, thereby carrying the pin and the connected actuator rod 134, downward, simultaneously compressing metering bell spring 162. Since the nibs 152 on the actuator rod are in contact with the surface of the closure plunger 62 contiguous with its bore 148, the continued downward movement of the actuator rod carries the plunger downward and out of the outlet 92 from the phantom line position shown in FIG. 7 to the extended or release position shown therein. The downward movement is completed when sleeve flange 224 bottoms out on flange 183 of the housing shell 180, thus preventing overtravel of sleeve-cam assembly 218 and damage to cam follower pin 174 of actuator assembly 64.

Once the seal between the top surface 142 of the closure plunger 62 and the outlet 92 has been broken, the particulate material 26 is free to drop out of the outlet, through the funnel neck 94 and out of the dispensing unit.

The reaching of the release position as described immediately above marks the end of the downstroke of the dispensing unit.

The sealing of the outlet 92 and the reestablishment of the metering bell in any charging position, be it the same charging position or a different one, is accomplished by the upward movement of the actuator assembly 64. The upward movement, or upstroke, of the actuator assembly occurs in two separate and distinct steps. The first step, which concludes one operating cycle of the dispensing unit, occurs automatically upon release of the skirt 236 of the sleeve-cam assembly 218 after the material has been dispensed and is characterized by the actuator assembly carrying the closure plunger 62 back into the funnel outlet 92 to seal it while the metering bell 60 remains in the closed position. The second step or portion of the upstroke marks the initiation of another cycle of operation and, as such, requires user initiation.

The second step is characterized by the actuator assembly carrying the metering bell 60 from the closed position shown in FIG. 7 up to the charging position, such as shown in FIG. 6, which has been established by the rotation of the funnel unit as described heretofore.

Operation of the first step of the upstroke is as follows:

The release of the skirt 236 of the sleeve-cam assembly by the user enables the sleeve compression spring 228, along with the bell spring 162 (which had been compressed during the downstroke as shown in FIG. 7) to apply a simultaneous upward force to the flange 224 of the sleeve-cam assembly and the stop washer 164 linked to the actuator assembly by the cotter pin 166. This combined action causes the sleeve-cam assembly, and the actuator assembly, to move upward. The upward movement of the actuator rod 134 is coupled to the closure plunger 62, via closure plunger spring 154 which is linked to the actuator rod by retaining ring 156, whereupon the plunger moves upward until its conical top surface 142 makes contact with the portion of the funnel unit 58 contiguous with the outlet 92 (as shown by phantom lines in FIG. 7), thereby effectively sealing the outlet. Continued upward movement of the sleeve-cam assembly, and hence the actuator assembly and metering bell mounted thereon, is precluded by the automatic operation of the trigger 214 as it intercepts the upward moving sleeve-cam assembly. This action marks the end of one complete cycle of the operation of the dispensing unit.

As noted heretofore, when the trigger intercepts the upward movement of the sleeve-cam assembly, the dispensing unit will have completed one cycle of operation. Since the closure plunger is now seated within the outlet, and since the metering bell is also closed, that is, in contact with the funnel, a double seal against the ingress of moisture is created so that the apparatus will maintain the freshness of the product within the jar for an extended period of time.

An additional advantage of the interruption of the travel of the sleeve-cam assembly by the trigger 214 is the fact that the funnel unit may be left at its previous setting to recharge the cavity 132 with an identical amount of material when the trigger is tripped, or it can be turned clockwise to reduce the volume of the succeeding portion, or counterclockwise to increase the volume of the succeeding portion, all before the initiation of the next cycle of operation.

To initiate the new cycle of operation, the user merely applies a slight upward force to the end of the actuating lever 260 of the trigger. This action pivots the latching section 262 of the trigger about the portion of the housing sidewall contiguous with the opening 212 against the bias of the spring finger 264 until the end 266 of the latching section fully enters the notch 268 in the sleeve's flange 224. Once this occurs the sleeve is released, whereupon the compression spring 228 moves the sleeve-cam assembly upward, thereby carrying the actuator assembly mounted metering bell 60 to the charging position as described heretofore.

It is important to note that the interception of the upward movement of the sleeve-cam assembly by the trigger pacifies the receiver housing assembly, which is to say the assembly no longer acts in any way on the funnel unit, or the assemblies disposed therein. The funnel unit may be turned to zero (0) and removed from the receiver housing assembly or alternately, it may be turned to any setting position through its 90° range without being acted upon by the receiver housing except insofar as the locking tabs 210 secure the funnel unit 58 within the receiver. As will be seen from the phantom lines in FIG. 7 showing the 'latched' sleeve-cam assembly, the dump ring 246 has moved upward to a point where the cam follower 174 of the actuator assembly itself is pacified, with the bell spring 162 having lifted the actuator assembly and consequently the closure plunger 62 thereon up into funnel outlet 92 where it is secured by the spring bias of the actuator assembly 64 as described heretofore. The opposing ends of the cam follower 174 are not acted upon by the cam tracks 242 of the sleeve-cam assembly 218 until such time as the trigger 214 is tripped. At that time, the sleeve-cam assembly moves upward and the cam tracks intercept the cam follower, thereby raising the actuator assembly 64, and the metering bell disposed thereon within the funnel unit to a height consistent with cam setting. The maximum upward travel of the sleeve-cam assembly is reached when the cam skirt 236 contacts the housing shell flange 186.

Figure 10:
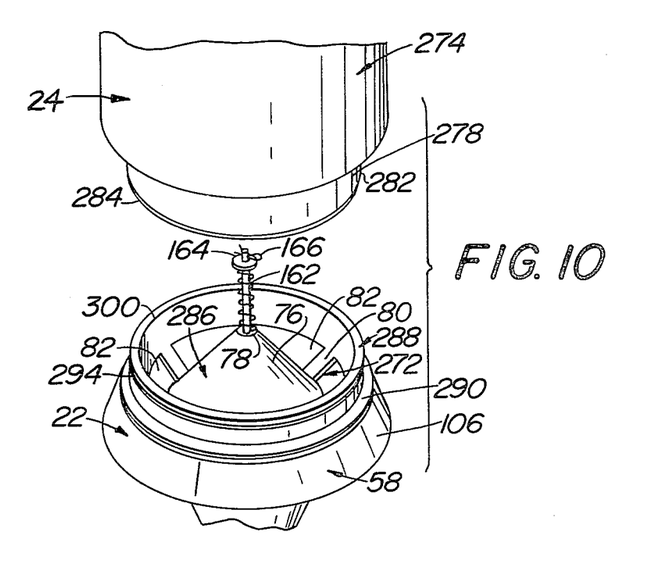
FIG. 10 is a partially exploded perspective view of a portion of an alternative embodiment of the apparatus of FIG. 1; and, FIG. 11 is an enlarged sectional view of the top portion of the apparatus shown in FIG. 10.
Figure 11:
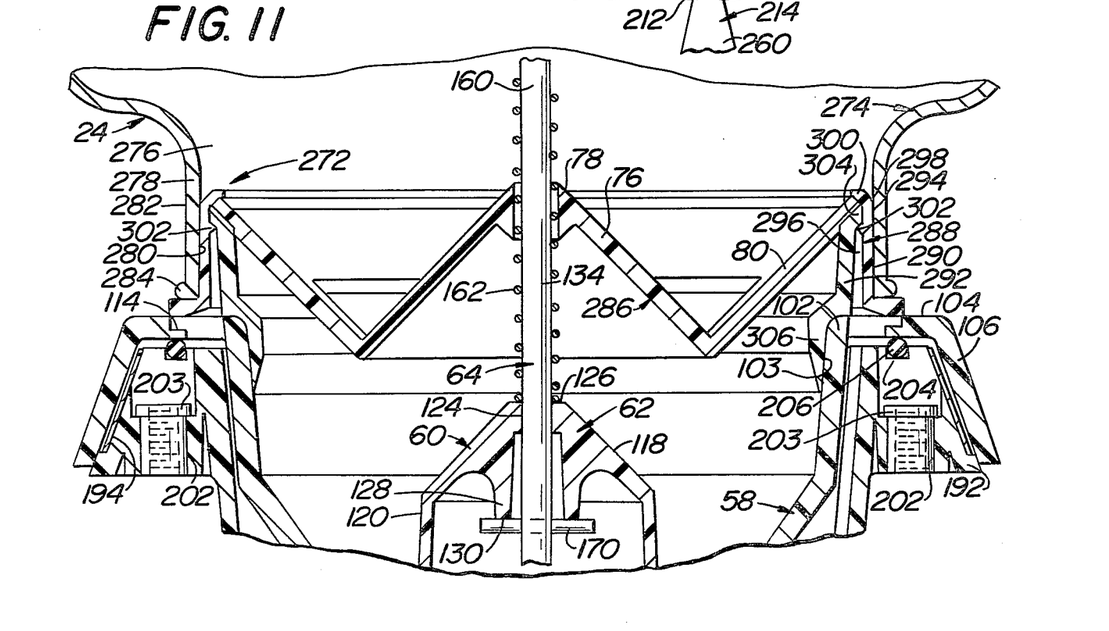

In FIGS. 10 and 11, there is shown a dispensing unit 22 of the instant invention but with an alternative embodiment of a flow control-adapter assembly 272 for use with a seal-bowl type storage vessel 274 like that sold by Anchor Hocking Glass Corp. As can be seen, the bowl 274 is in the form of a cylindrical glass container having a mouth 276. The mouth is formed of a cylindrical side wall 278 whose inside surface 280 is smooth and whose outside surface 282 terminates in a peripheral lip 284. The assembly 272 comprises a flow control disc 286 and an adapter ring 288. The flow control disc 286 is identical in construction to the flow control disc 70 described heretofore, except that the disc 286 does not include any horizontal peripheral flange projecting from the edge of the angularly extending flange portion 80.

The adapter ring 288 is made up to two elements, namely, an outer seal ring 290 and an inner ring 292. The outer seal ring 290 is hollow and is arranged for insertion within the mouth 276 of the bowl 274. The outside diameter of the ring is at least as large as the inside diameter of the mouth and the ring is formed of a resilient, food grade, plastic material such that when inserted within the mouth of the bowl its outside surface 294 frictionally engages the inside surface 280 of the bowl's mouth. The inside surface 296 of the outer seal ring 290 includes an annular groove 298 extending about the entire ring and disposed closely adjacent to the top edge thereof. The groove is formed between a pair of ribs 300 and 302. The rib 300 projects radially inward and extends about the entire periphery of the inner ring 292. The lower rib 302 also extends fully about the ring and projects inward radially.

The inner ring 292, like the outer seal ring, is a hollow member. The top peripheral edge of the inner ring is in the form of an outward angularly extending flange 304 which is located and secured within the groove 298 of the outer seal ring. The peripheral edge of the flange 80 of the flow control disc 286 is connected to the top edge of the inner ring 292 and is also located within the groove 298. The upper rib 300 of the outer seal ring overhangs the top peripheral edge of the flow control disc flange 80 to insure that the flow control disc is held firmly in place.

The bottom of the inner ring is in the form of an offset cylindrical wall portion 306 which is identical in construction to the corresponding portion 87 of the adapter ring 68 described heretofore and is arranged to be frictionally secured and welded within the mouth of the funnel unit 58 to firmly connect the adapter ring 288 and the bowl 274 secured thereto onto the dispenser unit 22.

As should be appreciated from the foregoing, the dispenser unit of the instant invention can be fixed or portable, can be manually operated, or, without modification, be electromechanically operated. The dispensing device provides a practical means of accurately predetermining the volume of particulate material to be dispensed. The accuracy of the dispensing operation is achieved irrespective of the amount of material stored within the device, by intercepting the bulk of the material with a flow control disc at a point that permits adjustable control of the angle of repose of the downstream material flowing within the dispensing unit. The ability to precisely adjust the quantities of the material to be dispensed by the apparatus is of considerable importance since it enables the user to select the setting most desirable for his or her taste and without requiring electrical or electromechanical programming. In addition, there is no need for special skills to set and maintain or reset the quantity adjustment.

Furthermore, the construction of the dispensing unit facilitates its ready assembly and disassembly for cleaning or repair.

In addition, by the mere selection of a suitable adapter the dispenser can be utilized to dispense particulate material from the various types of containers in which such materials are sold, e.g., 70mm glass jars, 4 inch diameter cans, or 4 inch diameter glass bowls for table use, or any other container in which such materials are sold.

Maximum protection from the effects of humidity is a benefit inherent in the operation of the dispensing device since the trigger and latching means insures that the metering bell remains in the closed position automatically after the dispensing operation and the closure plunger is returned to the funnel dispensing outlet. This feature is of considerable important for while some traditional prior art systems leave the product committed to the next cycle exposed to the atmosphere at the dispenser outlet, the dispensing by the instant apparatus provides two humidity barriers, namely, the closure plunger and the closed metering bell.

It should be pointed out at this juncture that while the apparatus 20 shown herein represents the first practical apparatus for in-home use it can, without modification, be used in commercial, institutional and vending configurations, conferring benefits to each heretofore unrealized by prior art.

For those applications where fast product turnover is anticipated, and where rapid delivery of servings of constant volume is important, as in fast food systems, the trigger 214 may be removed from the receiver housing assembly 56, and the dispensing unit 22 will automatically recharge to the previous constant setting, at the end of each cycle.

The trigger 214 is removed from the receiver housing assembly 56 by pulling downward on the skirt 236 of the cam element 222 until sleeve-flange 224 bottoms out on shell housing flange 183, and holding it there. Pressing down on lever section 260 of trigger 214 causes the trigger latching section 262 and spring finger 264 associated therewith to arc upward and inward toward the housing central axis and thereby release the spring finger tip from sleeve trigger notch 268, whereupon the trigger can be threaded outward through trigger opening 212 in wall 182 of housing shell 180. The lifetime flexibility of molded DELRIN spring finger 264 is such that the trigger 214 may be simply replaced by reversing the procedure noted herein while guiding the spring finger tip back into the aperature provided by sleeve trigger notch 268 and the housing inner wall 270 adjacent to flange 183.

Where supplementary warm dry air environments are provided according to existing art for commercial applications it will be readily seen that apparatus 20 may have 'adapted' to it, a 4 inch tubular sleeve and lid thereon, to form a canister typical of applications where a preferred embodiment of the said invention requires product first in, to be product first out on a continuing basis.

Without further elaboration, the foregoing will so fully illustrate my invention that others may, by applying the current or future knowledge, readily adapt the same for use under various conditions of service.

What is claimed and desired to be secured by Letters Patent is:

1. A cyclically operable mechanism for dispensing measured quantities of a flowable material from a reservoir of such material comprising:
   a funnel having an inlet, an outlet smaller than said inlet, and an interior wall tapering from said inlet to said outlet;
   a reciprocable rod extending through said outlet;
   a metering member mounted above said outlet on said rod for relative movement with respect to said rod between a charging position, in which said metering member is spaced a predetermined distance from said interior wall, and a dispensing position in which said metering member abuts said interior wall to form a dispensing chamber therewith;
   a closure member mounted below said outlet on said rod for relative movement with respect to said rod between a closed position, in which said outlet is closed, and an open position in which said outlet is opened;
   means, operatively connected to said rod, for reciprocating said rod from an upper position, in which said metering member is in said charging position and said closure member is in said closed position, through a first intermediate position, in which said metering member is in said dispensing position and said closure member is in said closed position, through a second intermediate position, in which said metering member is in said dispensing position and said closure member is in said open position, to a final position in which said metering member is in said dispensing position and said closure member is in said closed position; and means, operatively connected to said rod, for recycling said rod to said upper position.

2. A cyclically operable mechanism according to claim 1 further including:

means, operatively connected to said rod, for selectively varying said predetermined distance between said interior wall and said metering member.

3. A cyclically operable mechanism according to claim 2 further including:

means, removably connected to said rod above said metering member, for shielding said metering member.

4. A cyclically operable mechanism for dispensing measured quantities of a flowable material from a reservoir of such material comprising:

a housing having top and bottom openings;

a sleeve movably mounted inside said housing for upward and downward motion between an upper, an intermediate and a lower position with respect to said housing;

means, connected to said sleeve, for urging said sleeve into its upper position;

latching means movably mounted on said housing for movement between a first position, in which said latching means permits the upward movement of said sleeve, and a second position in which said latching means prevents the upward movement of said sleeve and holds said sleeve at said intermediate position;

a funnel rotatably mounted on said housing, said funnel having an inlet and an outlet;

a reciprocable stem disposed within the funnel and passing through the funnel outlet;

a helical camming surface secured to the interior of said sleeve;

a cam follower fixedly secured to the lower end of said stem, operatively connected to said funnel for movement therewith and in engagement with said camming surface when said sleeve is in its upper position;

engagement means, secured to said sleeve a predetermined distance above said helical camming surface, for engaging said cam follower and for moving same downwardly during the downward motion of said sleeve;

an upper closure member operatively connected to said stem above said funnel outlet and movable between a charging position, in which said upper closure member is spaced from the wall of said funnel a distance determined by the position of the cam follower on the helical camming surface when said sleeve is in its upper position, and a metering position, in which said upper closure member abuts the wall of said funnel to form a dispensing chamber therewith when said latching means is in its second position; and a lower closure member operatively connected to said stem below said funnel outlet and movable between a closed position, in which said funnel outlet is closed when said sleeve is in said upper position and when said sleeve is in said intermediate position, and an opened position in which said funnel outlet is opened after the sleeve has moved downwardly a distance equal to or greater than said predetermined distance.

5. A cyclically operable mechanism according to claim 4 further including:

flow control means, removably connected to said stem above said upper closure member, for shielding said upper closure member.

6. A cyclically operable mechanism according to claim 5 further including:

first biasing means, operatively connected to said stem, for urging said cam follower into abutment with said helical camming surface; and second biasing means, operatively connected to said stem, for urging said upper closure member downwardly.

7. A cyclically operable mechanism for dispensing measured quantities of a flowable material from a reservoir of such material comprising:

a housing having annular top and bottom openings and provided with an internal annular shoulder adjacent said bottom opening;

a cylindrical sleeve movably mounted within said housing for axial motion with respect thereto and provided with upper and lower external annular shoulders;

two opposing helical camming surfaces secured to the interior of said sleeve;

two opposing arcuate shoulders secured to the interior of said sleeve a predetermined distance above said camming surfaces;

a compression spring surrounding said cylindrical sleeve and having its upper end in abutment with the external upper annular shoulder of said sleeve and its lower end in abutment with the internal annual shoulder of said housing;

a latch movably mounted on said housing for movement between a first position, in which said latch does not engage said sleeve, and a second position, in which said latch engages said sleeve to prevent the upward axial movement thereof;

a funnel rotatably mounted on said housing, said funnel having an inlet and an outlet;

an elongated tube fixedly secured to the exterior lower end of said funnel and provided with two opposing axially extending slots in the walls thereof.

an elongated vertically reciprocable stem disposed within the funnel and passing through said funnel outlet;

a horizontally oriented rod fixedly secured to the lower end of said stem, the ends of said rod passing through the slots in said tube and engaging said helical camming surfaces when said sleeve is in a first predetermined position with respect to said housing and engaging said arcuate shoulders when said sleeve has reached or exceeded a second predetermined position with respect to said housing;

an upper closure member operatively connected to said stem above said funnel outlet and movable between a charging position, in which said upper closure member is spaced from the wall of said funnel a distance determined by the position of the ends of the rod on the helical camming surface when said latch is in its first position, and a metering position, in which said upper closure member abuts the wall of said funnel to form a dispensing chamber therewith when said latch is in its second position; and a lower closure member operatively connected to said stem below said funnel outlet and movable between a closed position, in which said funnel outlet is closed when said sleeve is in said first predetermined position with respect to said housing, and an opened position in which said funnel outlet is opened when said sleeve has reached or exceeded said second predetermined position with respect to said sleeve.

8. A cyclically operable mechanism according to claim 7 further including:

biasing means operatively connected to said stem for urging said rod ends into abutment with said camming surfaces.

9. A cyclically operable mechanism according to claim 8 further including:

a flow control shield removably connected to said stem above said upper closure member, said shield having a plurality of apertures therein.

* * * * *